United States Patent [19]

Knifton et al.

[11] Patent Number: 4,543,411

[45] Date of Patent: Sep. 24, 1985

[54] PROCESS FOR SELECTIVE PREPARATION OF SECONDARY AND TERTIARY AMINES

[75] Inventors: John F. Knifton; David C. Alexander, both of Austin, Tex.

[73] Assignee: Texaco Inc., White Plains, N.Y.

[21] Appl. No.: 550,345

[22] Filed: Nov. 10, 1983

[51] Int. Cl.[4] .................... C07D 295/04; C07C 85/00
[52] U.S. Cl. .................................. 544/178; 548/579; 564/305; 564/398; 564/446; 564/467; 564/473; 564/499
[58] Field of Search ............... 564/467, 499, 305, 398, 564/446, 1, 473; 544/178; 548/579

[56] References Cited

U.S. PATENT DOCUMENTS

| | | | |
|---|---|---|---|
| 4,179,469 | 12/1979 | Imai | 564/467 |
| 4,298,541 | 11/1981 | Oswald et al. | 260/429 R |
| 4,299,985 | 11/1981 | Knifton et al. | 564/473 |
| 4,448,996 | 5/1984 | Yanagi et al. | 564/467 |

Primary Examiner—Charles F. Warren
Assistant Examiner—John A. Sopp
Attorney, Agent, or Firm—Jack H. Park; Kenneth R. Priem; Cynthia L. Kendrick

[57] ABSTRACT

Secondary and tertiary amines are selectively prepared by a process comprising reacting an olefin, a nitrogen-containing compound and synthesis gas in the presence of a catalyst system comprising a ruthenium-containing compound mixed with a quaternary onium salt, optionally in the presence of a solvent, heating the resultant mixture to a temperature of at least 100° C. and a pressure of at least 100 psi until there is substantial formation of the desired tertiary amine and separating the desired amine by a phase separation technique.

24 Claims, No Drawings

PROCESS FOR SELECTIVE PREPARATION OF SECONDARY AND TERTIARY AMINES

FIELD OF THE INVENTION

This invention relates to an aminomethylation process and more particularly this invention relates to the selective preparation of secondary and tertiary amines from olefins, primary or secondary amines and synthesis gas in the presence of a catalyst system comprising a ruthenium-containing compound mixed in a quaternary phosphonium salt optionally in the presence of a solvent, heating the mixture to a temperature of at least 100° C. and a pressure of at least 100 psi until there is substantial formation of the desired secondary or tertiary amine and separating said amine product by a novel phase separation technique. The resulting alkylamines are useful as surfactants or surfactant precursors.

BACKGROUND OF THE INVENTION

The principle of obtaining amines starting from an olefin, hydrogen, carbon monoxide and a primary or secondary amine is known. Various techniques embodying this principle have been described using catalysts of various kinds.

Early work in this field taught that aliphatic acids may be obtained by reacting carbon monoxide with an olefin and steam and that ammonia may be reacted with carbon monoxide to produce formamide. U.S. Pat. No. 2,422,632 (1944) appears to be the first work to suggest a process by which an olefin may be reacted with carbon monoxide and ammonia or an amine having replaceable hydrogen to form an amide or amine.

U.S. Pat. No. 2,497,310 (1946) defined a process for the synthesis of aliphatic amines which consisted of introducing carbon monoxide, hydrogen, a compound from the group consisting of ammonia and amines having at least one hydrogen attached to amino nitrogen, an unsaturated compound containing a non-benzenoid double bond between carbon atoms, and a catalytic quantity of cobalt metal, into a pressure resistant vessel and heating the resultant mixture within the range of 50°–350° C. under a reaction pressure in excess of 50 atm, whereby a reaction product containing amines is produced and thereafter separated from the reaction product.

In Shell International Research Maatschappy B. V. Neth. Appl. No. 6,405,802 Nov. 30, 1964; U.S. Pat. No. 3,234,283 (1966) tertiary amines are obtained in improved yields and at lower pressures than prior process by treating CO, hydrogen and a secondary amine with a $C_{10}$–$C_{13}$ olefinic mixture in the presence of a cobalt carbonyl-trialkylphosphine catalyst.

U.S. Pat. No. 3,513,200 (1970) covers the utilization of Group VIII metal complexes bearing a biphyllic ligand such as a phosphine and, optionally, these complexes may contain a metal hydride complexed with CO. There can be added, as an adjuvant, poly(hetercyclo)amines. The reaction is realized at a temperature between 50° and 200° C. and under a pressure ranging from 5 to 300 atmospheres. A significant proportion of aldehydes is obtained and the selectivity to amines is still in this case very moderate.

In a paper by Iqbal published in Helvetica Chemica Acta, Volume 54, pages 1440 to 1445 (1971), as well as in U.S. Pat. No. 3,947,458 (1976), the catalytic aminomethylation of olefins is described employing a rhodium oxide catalyst, an iron carbonyl catalyst and a mixed rhodium oxide/iron carbonyl catalyst. (Rhodium carbonyls form during the reaction.) The overall reaction is described as follows:

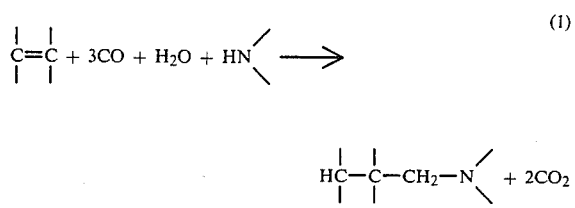

(1)

The mixed rhodium/iron carbonyl catalyst of Iqbal is said to be superior to the rhodium carbonyl catalyst alone and to the iron carbonyl catalyst alone. However, this mixed rhodium carbonyl/iron carbonyl catalyst is believed by Laine (U.S. Pat. No. 4,292,242) to be less selective and has other disadvantages, among which are the following: The rhodium carbonyl/iron carbonyl catalyst is not stable and is prone to decompose; its use results in carboxy amide by-products; and it reduces some of the intermediate aldehyde to an alcohol. Also, in the case of an olefin having a terminal vinyl group, $-CH=CH_2$, a considerable proportion of the amino product is branched chain, thus

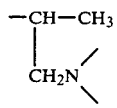

rather than straight chain, thus

The straight chain products are more important commercially.

U.S. Pat. No. 4,096,150 (1978) discloses a process for the manufacture of tertiary amines wherein an olefin, hydrogen, CO and secondary amine are reacted in the presence of a coordination complex catalyst of a Group VIII metal and a ligand, the donor atom of which is oxygen, nitrogen or sulfur.

In *J. Org. Chem.* 45 3370 (1980), Laine, et al. describe the results of their studies on the aminomethylation reaction using a variety of Group VIII transition-metal carbonyl catalyst precursors.

U.S. Pat. No. 4,292,242 states that the object of its invention is to provide improved methods of aminomethylation which are more selective and lead to fewer unwanted by-products such as alcohols and carboxy amides. A further object mentioned was to provide a more stable mixed carbonyl catalyst, the use of which would result in higher yields of the desired amines. Here the claimed catalyst is a mixed ruthenium carbonyl/iron carbonyl in a suitable solvent. Again, this process leads to a formamide by-product.

In *J. Org. Chem.*, 47, 445 (1982), Jachimowicz, et al. discuss the various approaches which have been used to attempt to devise a one-step, efficient and general conversion of olefins to amines. Among the catalysts used in processes devised by various people have been iron pentacarbonyl, rhodium oxide, ruthenium/iron carbonyl and iridium catalysts. The discussion in this article examines the feasibility of various aminomethylation syntheses.

In prior processes in the art by which aminomethylation takes place, the reaction must often take place at high temperatures and/or pressures, the olefin conversion and selectivity to the desired tertiary amines is not as high as desired, unwanted by-products such as formamides are often formed, and a high degree of desired linearity is not achieved. Additionally separation of the desired product from by-products is often difficult, expensive and time consuming; distillation as a separation technique can be relatively difficult because of the high boiling point of the products.

It would be a considerable advance in the art to devise a system for producing secondary and tertiary amines from CO, hydrogen, olefins and primary and secondary amines by an aminomethylation process which results in a product with a much higher percentage linear amines. The resulting alkylamines are useful as surfactants or surfactant precursors. In such applications the linear products are more desirable and, as stated, it would be a considerable advance to provide them in higher yield. In addition, it would be an advance over prior art to devise a process which proceeds under milder reaction conditions, forms fewer unwanted by-products such as formamides and affords easy and efficient separation of the desired product from by-products and catalyst.

SUMMARY OF THE INVENTION

These and other desirable results are achieved by the process of this invention comprising preparing secondary and tertiary amines by an aminomethylation process which comprises reacting an olefin, a nitrogen-containing compound selected from the group consisting of primary and secondary amines, and synthesis gas (a mixture of carbon monoxide and hydrogen) in the presence of a catalyst system comprising a ruthenium-containing compound mixed with a quaternary salt, optionally in the presence of a solvent, and heating the resulting mixture to a temperature of at least 100° C. and a pressure of at least 100 psi until there is substantial formation of the desired secondary or tertiary amine.

In the presence of certain added solvent media, the desired secondary or tertiary amine product is separated from said ruthenium catalyst by a useful phase separating technique, the efficiency of which is determined by the particular choice of solvent.

DETAILED DESCRIPTION OF THE INVENTION

In the broadest aspect of this invention secondary and tertiary amines are prepared from an olefin, synthesis gas (a mixture of carbon monoxide and hydrogen), and a nitrogen-containing compound selected from the group consisting of primary and secondary amines in the presence of a catalyst system comprising a ruthenium compound mixed with a quaternary salt, optionally in the presence of a solvent, heating the resultant mixture to a temperature of at least 100° C. and a pressure of at least 100 psi until there is substantial formation of the desired secondary or tertiary amine and optionally separating said amine products by a phase separation technique.

Aminomethylation reactions used in this invention to prepare secondary and tertiary amines from olefins, synthesis gas (CO/H$_2$) and primary or secondary amines can be represented by the following general equation:

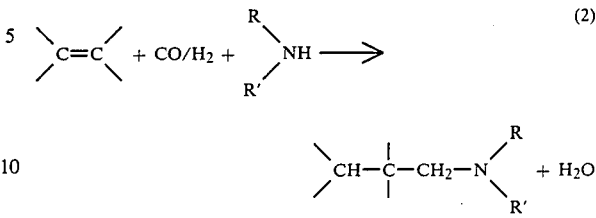

Here R and R' may be hydrocarbon groups containing from one to twenty carbon atoms. Alternatively, either R or R' (but not both) may be hydrogen. Formation of a less-desirable, branched-chain, amine product is illustrated by equation (3):

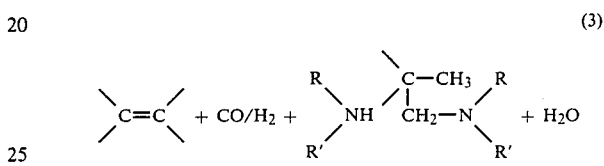

The olefin aminomethylation reaction is believed to proceed by way of an aldehyde intermediate. Accordingly, the starting material may be an aldehyde instead of an olefin. In this case the synthesis of secondary or tertiary amines may be described by the following general equation:

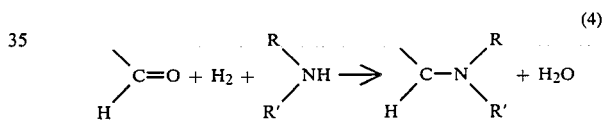

Again, R and R' may either be hydrogen, or both are hydrocarbyl groups each containing one to twenty carbon atoms.

In the process of this invention the ruthenium compound is dispersed in a quaternary phosphonium salt. This process is an improvement over prior work in the area and offers distinct advantages such as faster rate of reaction, higher degree of linearity and more flexibility. A ruthenium component is necessary in the practice of this invention in order to achieve the desired aminomethylation to secondary or tertiary amine. The quaternary phosphonium salt component ensures improved linearity of said secondary or tertiary amine product, in accordance with general equation (2).

In order to present the inventive concept in the greatest possible detail as to promote its understanding, the following supplementary disclosure is submitted.

A. CATALYST COMPOSITION

The catalyst components suitable in the practice of this invention essentially include a ruthenium-containing compound dispersed in a quaternary ammonium or phosphonium salt, optionally in the presence of a solvent from the group consisting of aliphatic and aromatic amides, ethers and hydrocarbons.

The actual catalytically active species is unknown but is believed to comprise ruthenium in complex combination with a quaternary phosphonium salt as well as carbon monoxide and hydrogen.

In the practice of this invention the ruthenium-containing catalyst, as well as the quaternary salt, may be chosen from a wide variety of organic and inorganic compounds, complexes, etc., as it will be shown and illustrated. It is only necessary that the catalyst precursor actually employed contain said metal in any of its ionic states.

The ruthenium catalyst precursors may take many different forms. For instance, the ruthenium may be added to the reaction mixture in an oxide form, as in the case of for example, ruthenium(IV) oxide hydrate, anhydrous ruthenium(IV) dioxide and ruthenium(VIII) tetraoxide. Alternatively, it may be added as the salt of a mineral acid, as in the case of ruthenium(III) chloride hydrate, ruthenium(III) bromide, ruthenium(III) iodide, tricarbonyl ruthenium(II) iodide, anhydrous ruthenium(III) chloride and ruthenium nitrate, or as the salt of a suitable organic carboxylic acid, for example, ruthenium(III) acetate, ruthenium naphthenate, ruthenium valerate and ruthenium complexes with carbonyl-containing ligands, such as ruthenium(III) acetylacetonate. The ruthenium may also be added to the reaction zone as a carbonyl or hydridocarbonyl derivative. Here, suitable examples include triruthenium dodecacarbonyl and other hydridocarbonyls such as $H_2Ru_4(CO)_{13}$ and $H_4Ru_4(CO)_{12}$, and substituted carbonyl species such as the tricarbonylruthenium(II) chloride dimer, $[Ru(CO)_3Cl_2]_2$.

Preferred ruthenium-containing compounds include oxides of ruthenium, ruthenium salts of an organic carboxylic acid and ruthenium carbonyl or hydridocarbonyl derivatives. Among these, particularly preferred are ruthenium (IV) dioxide hydrate, ruthenium tetraoxide, anhydrous ruthenium(IV) oxide, ruthenium acetate, ruthenium(III) acetylacetonate, and triruthenium dodecacarbonyl.

Especially good results were observed with triruthenium dodecacarbonyl and ruthenium oxide.

The quaternary onium salt to be used in the catalyst composition may be any onium salt but is preferably one of those containing phosphorus, such as those of the formula:

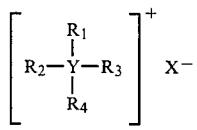

wherein Y is phosphorus, $R_1$, $R_2$, $R_3$ and $R_4$ are organic radicals, preferably alkyl, aryl or alkaryl radicals, and X is an anionic species. The organic radicals useful in this instance include those alkyl radicals having from 1 to 20 carbon atoms in a branched or linear alkyl chain, such as methyl, ethyl, n-butyl, isobutyl, octyl, 2-ethylhexyl and dodecyl radicals. Tetraethylphosphonium bromide and tetrabutylphosphonium bromide are typical examples presently in commercial production. The corresponding quaternary phosphonium acetates, nitrates, chromates, tetrafluoroborates and other halides, such as the corresponding chlorides, and iodides, are also satisfactory.

Equally useful are the phosphonium salts containing phosphorus bonded to a mixture of alkyl, aryl and alkaryl radicals, which radicals preferably contain from 6 to 20 carbon atoms. The aryl radical is most commonly phenyl. The alkaryl group may comprise phenyl substituted with one or more $C_1$ to $C_{10}$ alkyl substituents, bonded to phosphorus through the aryl function.

Illustrative examples of suitable quaternary onium salts include tetrabutylphosphonium bromide, heptyltriphenylphosphonium bromide, tetrabutylphosphonium iodide, tetrabutylphosphonium acetate, tetrabutylphosphonium nitrate, tetrabutylphosphonium chromate, tetraoctylphosphonium tetrafluoroborate, tetrahexylphosphonium acetate and methyl tri-n-butylphosphonium iodide.

The preferred quaternary onium salts and bases to be used in the process comprise the tetraalkylphosphonium salts containing alkyl groups having 1 to 6 carbon atoms, such as methyl, ethyl, butyl, hexyl, heptyl and isobutyl. Tetraalkylphosphonium salts, such as the halides, bromides, chlorides and iodides, and the acetate and chromate salts are the most preferred. Especially good results were observed with tetrabutylphosphonium bromide.

B. FEEDSTOCK

The feedstock used in the practice of this invention comprises an olefin, a nitrogen-containing compound from the group consisting of primary and secondary amines, carbon monoxide and hydrogen.

The process can be applied to any aliphatic olefin, including aliphatic monosubstituted, disubstituted and trisubstituted olefins containing 2 to 25 carbon atoms, as well as mixtures of the same. The process is particularly suited to the aminomethylation of terminal olefins containing 2 to 25 carbon atoms. Examples of suitable olefins include straight-chain terminal olefins such as propylene, 1-butene, 1-octene, 1-decene, 1-dodecene, 1-tetradecene, and 1-hexadecene. Also suitable are branched-chain, terminal olefins such as 3-methyl-1-pentene, 4-methyl-1-hexene, 3,3-dimethyl-1-butene and 3,4-dimethyl-1-hexene. Linear and branched, internal olefins are also suitable substrates for this aminomethylation. Examples include 2-octene, 3-octene, 4-octene, mixed internal octenes, mixed internal decenes, mixed internal dodecenes; as well as 2-pentene, 3-hexene, 5-decene, 2-decene, 2-dodecene, and 5-methyl-2-hexene. Cyclic olefins like cyclohexene, cyclopentene, cycloheptene and their branched derivatives such as 1-methylcyclohexene and 2-ethylcyclopentene are also useful in the practice of this invention. The process can also be applied to non-conjugated di-olefins containing 5 to 25 carbon atoms such as 1,7-octadiene.

Particularly preferred in the practice of this invention is the use of straight-chain terminal olefins such as propylene, 1-butene, 1-octene, 1-decene and 1-dodecene.

Alternatively, the secondary and tertiary aliphatic amine products may be produced from the corresponding aldehyde, instead of said olefins. These aldehydes would have the same carbon skeletal structures as the desired amine products, in accordance with the stoichiometry of equation 4.

Suitable nitrogen-containing coreactants useful in the practice of this invention include primary and secondary amines containing one to 40 carbon atoms. These amines may be straight or branched chain aliphatic series, they may be cycloaliphatic amines, or they may be aromatic amines. Examples of suitable primary aliphatic and aromatic amines include methylamine, ethylamine, n-propylamine, n-hexylamine, n-dodecylamine and aniline. Suitable cycloaliphatic amines include cyclohexylamine and cyclopentylamine. Secondary aliphatic amines that are satisfactory coreactants include dimethylamine, diethylamine, methylethylamine, di(n-propyl)amine, di(iso-propyl)amine, di(ethylhexyl)amine, piperidine, morpholine, di(n-methyl)amine, and di(n-decyl)amine, as well as 2-aminooctane, N-methylaniline and pyrrolidine. Aliphatic diamines such as piperazine are also useful in the practice of this invention.

The quantity of nitrogen-containing coreactant employed in the instant invention is not critical and may vary over a wide range. In general, however, it is desirable to conduct these synthesis in the presence of sufficient primary or secondary amine to satisfy the stoichiometry of equations (2), (3) and (4).

C. GAS

The relative amounts of carbon monoxide and hydrogen which can be initially present in the synthesis gas mixture are variable, and these amounts may be varied over a wide range. In general, the mole ratio of $CO:H_2$ is in the range from about 20:1 to about 1:20, and preferably from about 5:1 to 1:5, although ratios outside these ranges may also be employed with good results. Particularly in continuous operations, but also in batch experiments, the carbon monoxide-hydrogen gaseous mixtures may also be used in conjunction with up to 50% by volume of one or more other gases. These other gases may include one or more inert gases such as nitrogen, argon, neon, and the like, or they may include gases that may, or may not undergo reaction under carbon monoxide hydrogenation conditions, such as carbon dioxide, and hydrocarbons, such as methane, ethane, propane and the like.

D. SOLVENT

The reaction is optionally achieved in the presence of a suitable solvent, selected from the classes of organic solvents that include aliphatic amide solvents, aromatic amides, aliphatic and aromatic ether solvents and aromatic hydrocarbon solvents. These solvents should be liquids under the conditions of the aminomethylation reactions of equation (2), and should substantially solubilize the ruthenium compound and quaternary phosphonium salt catalyst components.

The important advantages of the added solvent are enhanced yields of desired amine, improved amine product linearity and in some cases, ease of separation of the desired secondary and tertiary amine product from the ruthenium catalyst through the formation of two-phase liquid products. The use of solvents is optional, but examples 11–19 will demonstrate that the use of solvent leads to improvements in both the yield and linearity of the desired amine.

Suitable amide solvents may be selected from the group of amides that includes N,N-dimethylformamide, N,N-dimethylacetamide, hydroxy-ethylpyrrolidone, N-methylpyrrolidone, N-isopropylpyrrolidone, N,N-diethylformamide, N,N-dimethylacetamide, N,N-dimethylbenzamide, N,N-diphenylformamide, N,N-dimethylbutyramide and N-benzylpyrrolidone.

Examples of suitable ether solvents include p-dioxane, tetrahydrofuran, tetrahydropyran, diethyl ether, diisopropylether, diphenyl ether, ethyleneglycol dimethyl ether, diethyleneglycol dimethyl ether and triethylene glycol dimethyl ether as well as mixtures thereof.

Suitable aromatic hydrocarbon solvents include toluene, o-xylene, p-xylene, mixed xylenes, mesitylene, ethylbenzene, benzene, substituted aromatics as well as mixtures thereof.

A preferred class of added solvents for aminomethylation includes N,N-dimethylformamide, N,N-dimethylacetamide, N-substituted pyrrolidones such as N-isopropylpyrrolidone and hydroxyethylpyrrolidone, ethers such as p-dioxane and aromatics such as toluene. The best results are obtained with dimethylformamide (DMF).

Some of the particular advantages noted when adding N,N-dimethylformamide (DMF) solvent to the reaction mixture include:

1. With N,N-dimethylformamide (DMF) as solvent the conversion and selectivity to linear tertiary amines are both higher than in the absence of the solvent, as will be demonstrated by Examples 9–11 in comparison to examples 1 and 6.

2. The liquid product cleanly separates into two phases, the upper layer of which is rich in amine product; the lower layer comprises DMF, unreacted primary and secondary amine, plus soluble ruthenium catalyst. These layers are easily separated. The lower layer, rich in catalyst, may be recycled.

The amount of solvent employed may vary as desired. In general, it is desirable to use sufficient solvent to fluidize the catalyst system.

E. CONCENTRATION

The quantity of ruthenium compound and quaternary onium salt employed in the instant invention is not critical and may vary over a wide range. In general, the novel process is desirably conducted in the presence of a catalytically effective quantity of active ruthenium species and of the quaternary onium salt which gives the desired product in reasonable yield. The reaction proceeds when employing as little as about $1 \times 10^{-6}$ weight percent and even lesser amounts, of ruthenium together with about $1 \times 10^{-6}$ weight percent or less quaternary onium salt, basis the total weight of the reaction mixture.

The upper concentration is dictated by a variety of factors including catalyst cost, partial pressure of carbon monoxide and hydrogen, operating temperature, etc. A ruthenium concentration of from about 0.0001 to about 1 weight percent in conjunction with a quaternary onium concentration of from about 0.001 to about 10 weight percent, based on the total weight of the reaction mixture is desirable in the practice of this invention. The preferred ruthenium to quaternary onium catalyst atomic ratio is from about 0.005 to about 0.2. Generally, in the catalyst system, the molar ratio of the ruthenium compound to the quaternary onium salt will range from about 1:5 to about 1:200. The especially preferred molar ratio is about 1:40.

F. TEMPERATURE

The temperature range which can usefully be employed in the process of the invention may vary over a considerable range depending upon experimental factors, including choice of catalyst, pressure and other variables. The process can take place at from 100° C. to about 300° C. or more. The preferred temperatures are above 120° C. and more preferably between 120° C. and 220° C. Coming under special consideration are temperatures ranging from 150° C. to 190° C.

G. PRESSURE

Superatmospheric pressures of about 100 psi or greater lead to substantial yields of the desired amines. A preferred range is from about 400 psi to about 4000 psi; although pressures above 4000 psi also provide useful yields of the desired products. A preferred range is from 500 psi to about 2000 psi.

The pressures referred to herein represent the total pressure generated by all the reactants although they are substantially due to the carbon monoxide and hydrogen reactants.

H. BY-PRODUCTS

The desired products of the reaction, the linear secondary and tertiary amines are formed in significant quantities varying from about 30% to about 90% in yield. Also formed will be minor by-products, such as alkanes, internal olefins and formamides as well as other branched-chain amine products. The desired secondary and tertiary amine products could be recovered from the reaction mixture by conventional means, such as fractional distillation in vacuo, etc., but distillation could be relatively difficult in some cases because of the high boiling point of the products.

This invention demonstrates that ruthenium compounds dispersed in onium salts, which are active catalysts in, for example, CO hydrogenation reactions, can be used in an aminomethylation reaction to allow for easy and efficient isolation of the product because it is simply a matter of separating the catalyst/salt phase from the amine product phase.

Further, in the process of this invention it has been discovered that an amide solvent, such as N,N-dimethylformamide, can be added to the reaction mixture of the aminomethylation reaction to increase rate of reaction, olefin conversion and selectivity to the desired linear products. This process allows for a useful phase separation technique which works well in separating the product amines from the ruthenium-onium catalyst. The crude reaction product mixture consists of two layers and the product amine is isolated from the upper, catalyst-free, layer.

I. INTRODUCTION OF CATALYST

The process of the invention can be conducted in a batch, semi-continuous or continuous manner. The catalyst can be initially introduced into the reaction zone batchwise, or it may be continuously or intermittently introduced into such a zone during the course of the synthesis reaction. Operating conditions can be adjusted to optimize the formation of the desired linear secondary or tertiary amines and said material can be recovered by methods known to the art, such as distillation, fractionation, extraction and the like. A fraction rich in the catalyst components may then be recycled to the reaction zone, if desired, and additional amine product generated.

J. IDENTIFICATION TECHNIQUES

The products have been identified in this work by one or more of the following analytical procedures; viz, gas-liquid chromatography (glc), infrared (ir), mass spectrometry, nuclear magnetic resonance (nmr) and elemental analyses, or a combination of these techniques. All temperatures are in degree centigrade and all pressures in pounds per square inch (psi).

Yields of secondary and tertiary amine products have been estimated in accordance with equation (2) through (4), basis the quantity of olefin or aldehyde converted, and expressed as a percentile. The figures are estimated from gas-liquid chromatography data.

The linearity of the amine products has been estimated by measuring the quantity of linear amine formed in accordance with equation (2), divided by the total secondary or tertiary amine formed on the basis of equation (2) and (3). Linearity is also expressed as a percentile.

To illustrate the process of the invention, the following examples are given. It is to be understood, however, that the examples are given in the way of illustration and are not to be regarded as limiting the invention in any way.

EXAMPLE I

This example demonstrates the preparation of dialkylundecylamines. A 300 ml stirred autoclave was charged with 17.0 g (121 mmol) 1-decene, 17.7 g (242 mmol) diethylamine, 0.047 g (0.25 mmol) ruthenium oxide hydrate, and 2.0 g (5.90 mmol) tetrabutylphosphonium bromide. The autoclave was sealed and purged with $\frac{1}{2}$ $CO/H_2$ by twice pressurizing to 200 psi and depressurizing. It was then pressurized to 600 psi with $\frac{1}{2}$ $CO/H_2$ and heated to 170°; this temperature was maintained for 6.5 hrs during which time the pressure fell from 820 psi to 700 psi. After cooling, the liquid product was withdrawn and found to consist of two layers—the upper layer was very light green and the lower layer was dark orange.

Gas chromatographic analysis of the upper layer showed the presence of:
38% diethylamine
2.7% decane
38% mixed decenes
21% undecyldiethylamines According to the criteria of equation (2) and (3), linearity of the undecyldiethylamines was 91%. Yield of undecyldiethylamines was 34%, basis decenes converted.

The bottom phase was primarily an aqueous phase containing <5% of the desired undecyldiethylamine product but a considerable fraction of the ruthenium catalyst originally charged.

EXAMPLE 2-5

Similar procedures were used to prepare the corresponding tertiary amines from 1-decene and dimethylamine, di-n-propylamine, and morpholine; a secondary amine was prepared from 1-decene and tert-butylamine. Results of these reactions are summarized in Table I.

TABLE I[a]

| Example | Primary & Secondary Amine Reactant | Secondary & Tertiary Amine Product Yield % | Linearity (%) |
|---|---|---|---|
| 2 | $Me_2NH$ | 31 | 89 |
| 3 | $n-Pr_2NH$ | 33 | 90 |
| 4 | $O(CH_2CH_2)_2NH$ | 47 | 93 |
| 5 | $t-BuNH_2$ | 36 | 98 |

[a]Reactions were as described in Example I except that $Ru_3(CO)_{12}$ (0.05 g, 0.23 mg atoms Ru) was used in place of $RuO_2$; in Example 5, 0.075 g $Ru_3(CO)_{12}$ and 1.0 g $Bu_4P^+Br^-$ were used.

The only other products seen in these reactions were internal decenes and small amounts (<4%) of decane.

EXAMPLE 6

This example demonstrates the lower product amine linearity observed during ruthenium-catalyzed aminomethylation in the absence of tetrabutylphosphonium bromide. A 300-ml stirred autoclave was charged with 17.0 g (121 mmol) 1-decene, 47 mg of ruthenium dodecacarbonyl, and 15 ml or 10.6 g (145 mmol) diethylamine. It was sealed and purged with $\frac{1}{2}$ CO/H$_2$ as described previously and then pressurized to 585 psi with $\frac{1}{2}$ CO/H$_2$. The mixture was heated to 160° C. and stirred for 5 hours during which time the pressure fell from 780 psi to 680 psi.

The estimated yield of undecyldiethylamines in this experiment was 37%; linearity of the amines was only 46%. This linearity figure is lower than is obtained in the corresponding Example I, where aminomethylation is conducted in the presence of tetrabutylphosphonium bromide.

EXAMPLE 7

This example demonstrates aminomethylation of internal olefins catalyzed by the ruthenium-quaternary phosphonium combination. Cyclohexene (9.9 g, 121 mmol) and pyrrolidine (17.9 g, 251 mmol) were charged to a 300 ml stirred autoclave, which was sealed and flushed with $\frac{1}{2}$ CO/H$_2$ as described in Example I. The mixture was pressurized to 550 psi and heated at 170° C. for 5.5 hours. The yield of cyclohexylmethyldiethylamine was found to be 11%.

EXAMPLE 8

This example shows that ruthenium-quaternary phosphonium salt catalyst can be used to prepare tertiary amines from aldehydes and secondary amines. Nonanal (17.4 g, 122 mmol), diethylamine (17.7 g, 241 mmol), Ru$_3$(CO)$_{12}$ (0.047 g, 0.22 mg-atoms Ru), and tetrabutylphosphonium bromide (2.1 g, 6.2 mmol) were charged to a 300 ml stirred autoclave which was sealed and purged as described in Example I. It was then pressurized to 600 psi with CO/H$_2$ $\frac{1}{2}$ and heated at 165° C. for approximately 1 hour. The yield of nonyldiethylamine was quantitative (>95%).

EXAMPLE 9

This example shows the enhancement of yield and amine linearity obtained when N,N-dimethylformamide (DMF) is present in the reaction mixture as a solvent. A 300 ml stirred autoclave was charged with 1-decene (12.6 g, 90 mmol), diethylamine (7.1 g, 97 mmol), DMF (10 ml), Ru$_3$(CO)$_{12}$ (0.070 g, 0.33 mg-atom Ru, and tetrabutylphosphonium bromide (1.5 g, 4.4 mmol). The reactor was sealed and flushed with $\frac{1}{2}$ CO/H$_2$ as described above, then pressurized to 500 psi and heated to 160° C. The reaction was continued for 4.5 hours with two repressurizations to 750 psi. The liquid product was two phases. In this case analysis of the top phase showed it to consist primarily of undecyldiethylamine product, unreacted diethylamine plus decenes, but <5% of the ruthenium catalyst originally charged. The yield of undecyldiethylamines was estimated to be 59% (basis decene converted) and its linearity (basis equations (2) and (3)) was 95%. The top layer also contained <6% DMF. The bottom layer comprised mainly DMF, unreacted decenes and diethylamine, and contained only 3% of the product undecyldiethylamines, but >95% of the ruthenium catalysts originally charged.

Both the undecyldiethylamine yield (59%) and linearity (95%) in this example are higher than those reported in Example I where the ruthenium-phosphonium salt catalyst is evaluated in the absence of dimethylformamide.

The product is isolated from the bulk of the ruthenium catalyst by separation of the two liquid product phases. The tertiary amine product may be isolated from the top phase by fractional distillation, or other suitable separation techniques well known in the prior art.

EXAMPLE 10

Example 10 shows that amine product linearity is increased by the presence of DMF even when tetrabutylphosphonium bromide is absent. The reaction was carried out as previously described with 14.8 g (105 mmol) 1-decene, 8.52 g (121 mmol) pyrrolidine, 10 ml DMF, and 0.08 g, Ru$_3$(CO)$_{12}$ (0.37 mg atoms Ru). Pressure was maintained at 700–750 psi and temperature at 155° C. for 3 hours. The yield of N-undecylpyrrolidine was found to be 46% and its linearity was 96%. This linearity figure (96%) is much higher than that found in Example 6, where ruthenium-catalyzed aminomethylation is conducted in the absence of both the DMF solvent and the tertbutylphosphonium bromide salt. Amine product yield is also higher in this example versus Example 6.

EXAMPLE 11

This example illustrates that dimethylacetamide is an equally suitable solvent for conducting ruthenium-catalyzed aminomethylations. The reaction was carried out as previously described in Example 9 with 1-decene (12.0 g, 90 mmol), diethylamine (7.1 g, 97 mmol), dimethylacetamide (10 ml), Ru$_3$(CO)$_{12}$ (0.08 g, 0.37 mg-atom Ru) and tetrabutylphosphonium bromide (1.2 g, 3.54 mmol). The pressure was maintained at 700–750 psi and the temperature at 150° C. for 3.5 hours. The yield of undecyldiethylamine was found to be 59% and its linearity was 97.7%.

EXAMPLE 12

Example 12 shows the application of this catalyst to reaction of a branched olefin. The reaction was carried out as previously described with 3,3-dimethyl 1-butene (7.8 g, 93 mmol), diethylamine (7.1 g, 97 mmol), DMF (10 ml), Ru$_3$(CO)$_{12}$ (0.1 g, 0.47 mg-atom Ru), and tetrabutylphosphonium bromide (1.3 g, 3.8 mmol). The pressure was maintained at 650–750 psi and the temperature at 160° for 3 hours. The yield of (4,4-dimethylpentyl)diethylamine was found to be 80% and its linearity was 100%.

EXAMPLE 13

In this example is illustrated the use of this catalyst system on reactions with a higher initial pressure. To a 180 ml glass liner was added 1-decene (5.2 g, 37 mmol), diethylamine (2.8 g, 39 mmol), DMF (4 ml), Ru$_3$(CO)$_{12}$ (0.040 g, 0.19 mg-atoms Ru), and tetrabutylphosphonium bromide (0.40 g, 1.18 mmol). The liner was transferred to a rocking autoclave where it was purged of air with 1/1 CO/H$_2$. The reaction was then carried out at 160° C. for 2 hours with an initial pressure of 1550 psi. The yield of diethylundecylamine was found to be 47%, and its linearity was 96%.

EXAMPLES 14–15

These examples demonstrate that N-substituted pyrrolidones are also suitable solvents for the reaction. The reactions were carried out as described in Example 9 with 12.6 g (90 mmol) 1-decene, 7.1 g (97 mmol) diethylamine, and 0.07, Ru$_3$(CO)$_{12}$ (0.33 mg-atom Ru). In Example 14, 10 ml N-isopropylpyrrolidone was employed as solvent and the yield of diethylundecylamine was 42%; its linearity was 92%. In Example 15, 10 ml hydroxyethylpyrrolidone was added as solvent and 1.1 g (3.2 mmol) tetrabutylphosphonium bromide was added also. In this example the diethylundecylamine yield was 42% and its linearity was 97%.

EXAMPLES 16–19

Examples 16–19 show the effect of added tetrabutylphosphonium bromide on aminomethylation reactions carried out in toluene and p-dioxane. These reactions were carried out as described in Example I with 11.1 g (79 mmol) 1-decene and 7.07 g (97 mmol) diethylamine in 10 ml of solvent. In all reactions 0.1 g Ru$_3$(CO)$_{12}$ (0.47 mg-atoms Ru) was used; in Examples 17 and 19 tetrabutylphosphonium bromide was added (1.0 g, 2.95 mmol). Results are summarized in Table II.

TABLE II[a]

| Example | Solvent | Bu$_4$PBr Added | Tertiary Amine Yield, % | Amine Linearity, % |
|---|---|---|---|---|
| 16 | Toluene | No | 19 | 61 |
| 17 | Toluene | Yes | 38 | 96 |
| 18 | p-Dioxane | No | 17 | 62 |
| 19 | p-Dioxane | Yes | 44 | 97 |

[a]Reactions were run at 150° for 5 hours at 500–700 psi

It may be noted from the data in Table II that both the yield and linearity of the amine product is higher in Examples 17 and 19 when tetrabutylphosphonium bromide is present, than in Examples 16 and 18 where the quaternary salt is absent.

What is claimed is:

1. A process for preparing secondary and tertiary amines which comprises reacting an olefin, a nitrogen-containing compound from the group consisting of primary amines and secondary amines, carbon monoxide and hydrogen in the presence of a catalyst system consisting of a ruthenium-containing compound from the group consisting oxides of ruthenium, ruthenium salts of a mineral acid, ruthenium salts of an organic carboxylic acid, ruthenium complexes with carbonyl-containing ligands, ruthenium carbonyls and hydridocarbonyls and substituted species thereof mixed with a tetraalkylphosphonium salt, optionally in the presence of a solvent heating the resultant mixture to a temperature of between 100° C. and 300° C. and a pressure of between 400 and 4000 psi until there is substantial formation of the desired secondary or tertiary amines and separating the resulting product.

2. The process of claim 1 wherein the olefin is a straight-chain terminal olefin containing 2 to 25 carbon atoms.

3. The process of claim 1 wherein the olefin is a branched-chain terminal olefin.

4. The process of claim 1 wherein the olefin is an internal olefin.

5. The process of claim 1 wherein the nitrogen-containing compound is a secondary amine.

6. The process of claim 5 wherein the secondary amine is selected from the group consisting of pyrrolidine, diethylamine, dimethylamine, morpholine and di-n-propylamine.

7. The process of claim 1 wherein the primary amine is selected from the group consisting of methylamine, ethylamine, n-hexylamine, and tert-butylamine.

8. The process of claim 1 wherein the process is conducted with a ratio of CO to H$_2$ of about 1:5 to 5:1.

9. The process of claim 1 wherein the ruthenium-containing compound is selected from the group consisting of ruthenium dioxide hydrate, ruthenium tetraoxide, anhydrous ruthenium(IV) oxide, ruthenium acetate, ruthenium(III) acetylacetonate and triruthenium dodecacarbonyl.

10. The process of claim 9 wherein the ruthenium-containing compound is selected from the group consisting of ruthenium(IV) oxide and triruthenium dodecacarbonyl.

11. The process of claim 2 wherein the straight-chain terminal olefin is selected from the group consisting of 1-octene, 1-decene, 1-dodecene, and propylene.

12. The process of claim 3 wherein the branched-chained terminal olefin is 3,3-dimethyl-1-butene.

13. The process of claim 1 wherein the tetraalkylphosphonium salt is selected from the group consisting of tetrabutylphosphonium bromide, tetrabutylphosphonium chloride, tetrabutylphosphonium iodide, tetrabutylphosphonium acetate and tetrabutylphosphonium chromate.

14. The process of claim 13 wherein the tetrabutylphosphonium salt is tetrabutylphosphonium bromide.

15. The process of claim 1 wherein a solvent is used which comprises an aromatic or aliphatic amide solvent.

16. The process of claim 15 wherein the amide solvent is selected from the group consisting of N-isopropylpyrrolidone, N-hydroxyethylpyrrolidone, N-methyl pyrrolidone and N,N-dimethylformamide.

17. The process of claim 16 wherein the amide solvent is N,N-dimethylformamide.

18. The process of claim 1 wherein an aromatic or aliphatic ether solvent is used.

19. The process of claim 18 wherein the ether solvent is selected from the group consisting of p-dioxane, tetrahydrofuran and diethyl ether.

20. The process of claim 1 wherein an aromatic hydrocarbon solvent is used.

21. The process of claim 20 wherein the aromatic hydrocarbon solvent is toluene.

22. The process of claim 1 wherein the preferred temperature range is from 120° C. to 220° C.

23. The process of claim 1 wherein the pressure is from 500 psi to 2000 psi.

24. A process for preparing secondary and tertiary amines comprising reacting an olefin, a nitrogen-containing compound, carbon monoxide and hydrogen in the presence of a catalyst system comprising a ruthenium compound, a quaternary phosphonium salt and an amide solvent, heating the resultant mixture to a temperature of at least 120° C. and a pressure of at least 500 psi until there is substantial formation of the desired tertiary amine product, allowing then the separation of the reaction mixture into two distinct phases consisting of an upper phase containing the product amine and a lower phase containing the reusable catalyst, by-products and other substances, removing the upper phase, and recovering the desired secondary or tertiary amine product.

* * * * *